(12) United States Patent
Masuda et al.

(10) Patent No.: US 9,710,605 B2
(45) Date of Patent: Jul. 18, 2017

(54) MEDICAL EQUIPMENT INFORMATION MANAGEMENT SYSTEM AND CONTROL METHOD FOR MEDICAL EQUIPMENT INFORMATION MANAGEMENT SYSTEM

(75) Inventors: Akira Masuda, Ashigarakami-gun (JP); Yuuichi Tada, Ashigarakami-gun (JP); Yuusuke Sekine, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 656 days.

(21) Appl. No.: 13/807,238

(22) PCT Filed: Jun. 28, 2011

(86) PCT No.: PCT/JP2011/003682
§ 371 (c)(1),
(2), (4) Date: Mar. 18, 2013

(87) PCT Pub. No.: WO2012/001950
PCT Pub. Date: Jan. 5, 2012

(65) Prior Publication Data
US 2013/0173288 A1    Jul. 4, 2013

(30) Foreign Application Priority Data
Jun. 30, 2010    (JP) .................................. 2010-149978

(51) Int. Cl.
*G06F 19/00* (2011.01)
*G06Q 50/22* (2012.01)
(Continued)

(52) U.S. Cl.
CPC ......... *G06F 19/3412* (2013.01); *G06Q 10/10* (2013.01); *G06Q 10/20* (2013.01); *G06Q 50/22* (2013.01)

(58) Field of Classification Search
CPC ...... G06Q 50/22; G06Q 50/24; G06F 19/322; G06F 19/323–19/327
(Continued)

(56) References Cited

U.S. PATENT DOCUMENTS

2001/0054082 A1* 12/2001 Rudolph ........... G06F 17/30876
709/217
2002/0188561 A1* 12/2002 Schultz .............. G06Q 10/0837
705/40
(Continued)

FOREIGN PATENT DOCUMENTS

EP    1 618 852 A1    1/2006
JP    11-065797 A    3/1999
(Continued)

OTHER PUBLICATIONS

International Search Report (PCT/ISA/210) issued on Jul. 26, 2011, by the Japanese Patent Office as the International Searching Authority for International Application No. PCT/JP2011/003682.
(Continued)

*Primary Examiner* — Luke Gilligan
*Assistant Examiner* — Jason Tiedeman
(74) *Attorney, Agent, or Firm* — Buchanan Ingersoll & Rooney PC

(57) ABSTRACT

A medical equipment information management system includes a medical equipment information storage medium capable of storing and transmitting medical equipment information and disposed in a packing unit configured to package medical equipment, a medical equipment information reception block configured to receive the medical equipment information transmitted from the medical equipment information storage medium, and a display unit configured to display the medical equipment information received by the medical equipment information reception block, wherein the
(Continued)

medical equipment information storage medium cannot transmit the medical equipment information when the packing unit is in a non-opened state, but is placed into a state in which it can transmit the medical equipment information if the packing unit is opened.

11 Claims, 12 Drawing Sheets

(51) Int. Cl.
*G06Q 10/10* (2012.01)
*G06Q 10/00* (2012.01)

(58) Field of Classification Search
USPC .......................................................... 705/2, 3
See application file for complete search history.

(56) References Cited

U.S. PATENT DOCUMENTS

| | | | |
|---|---|---|---|
| 2005/0004559 A1* | 1/2005 | Quick ................... | A61B 10/02 606/1 |
| 2006/0016897 A1* | 1/2006 | Yasuda .................. | A61B 50/30 235/492 |
| 2007/0245258 A1* | 10/2007 | Ginggen ............ | A61M 5/14276 715/772 |
| 2009/0099876 A1* | 4/2009 | Whitman .............. | G06F 19/327 705/3 |
| 2011/0148602 A1* | 6/2011 | Goh ...................... | G01S 5/0252 340/10.41 |

FOREIGN PATENT DOCUMENTS

| | | |
|---|---|---|
| JP | 2006-039773 A | 2/2006 |
| JP | 2006-178736 A | 7/2006 |
| JP | 2009-134515 A | 6/2009 |
| WO | 02/095675 A1 | 11/2002 |
| WO | 03/090663 A1 | 11/2003 |
| WO | 2004/008387 A1 | 1/2004 |

OTHER PUBLICATIONS

Office Action issued on Jun. 11, 2014, by the Japanese Patent Office in corresponding Japanese Patent Application No. 2010-149978. (2 pages).

Supplementary European Search Report issued Mar. 14, 2016 by the European Patent Office in corresponding European Application No. 11 80 0420.

* cited by examiner

MEDICAL EQUIPMENT INFORMATION MANAGEMENT SYSTEM AND CONTROL METHOD FOR MEDICAL EQUIPMENT INFORMATION MANAGEMENT SYSTEM

TECHNICAL FIELD

The present invention relates to a medical equipment information management system and a medical equipment information management method for managing medical equipment information such as, for example, an instruction manual.

BACKGROUND ART

Conventionally, in regard not only to medical equipment but also to a home appliance or the like, an instruction manual made of paper is provided to a user together with the equipment for the convenience to the user.

However, the amount of description of equipment increases together with sophistication of the equipment and so forth, and there is a problem that, if an instruction manual is appended in paper to the equipment, then it becomes less easy for the user to handle.

Therefore, for example, a configuration has been proposed wherein an instruction manual is built in a product such that a user of the equipment causes the data of the built-in instruction manual to be displayed on separate outputting equipment as occasion demands (refer to Patent Document 1).

In this manner, in the case of a home appliance or the like, it is sufficient if the user refers to the built-in instruction manual as occasion demands. However, for example, in the case of medical equipment used in a hospital or the like, it is demanded for a health care worker or the like who tries to use the medical equipment to confirm the instruction manual appended to the medical equipment.

Therefore, it is not preferable to build in an instruction manual in a product as in a home appliance, and an instruction manual of paper is still appended to medical equipment.

PRIOR ART DOCUMENT

Patent Document

Patent Document 1: Japanese Patent Laid-Open No. Hei 11-65797

SUMMARY OF THE INVENTION

Technical Problem

However, in medical equipment, similarly as in a home appliance or the like described above, the amount of contents of an instruction manual increases together with sophistication of the function and so forth. Further, since medical equipment is provided to all over the world, it is necessary to translate and print also the instruction manual into various languages of various countries and append the same to the medical equipment.

Therefore, there is a problem that enormous labor is required for preparation, printing, appending, management and so forth of the instruction manual to be appended to the medical equipment and the burden on the fabrication cost, management cost and so forth increases excessively.

Therefore, it is an object of the present invention to provide a medical equipment information management system and a medical equipment information management method wherein medical equipment information can be appended easily to medical equipment at a low cost while confirmation of medical equipment information such as an operation manual by a user and so forth are assured.

Technical Solution

According to the present invention, the object described above is achieved by a medical equipment information management system, including a medical equipment information storage medium capable of storing medical equipment information therein and transmitting the stored medical equipment information and disposed in a packing unit configured to package medical equipment, a medical equipment information reception block configured to receive the medical equipment information transmitted from the medical equipment information storage medium, and a display unit configured to display the medical equipment information received by the medical equipment information reception block, wherein the medical equipment information storage medium cannot transmit the medical equipment information when the packing unit is in a non-opened state, but is placed into a state in which the medical equipment information storage medium can transmit the medical equipment information if the packing unit is opened.

With the configuration described above, in response to opening of the packing unit, the medical equipment information (instruction manual information and so forth) is automatically transmitted from the medical equipment information storage medium to the medical equipment information reception block. The medical equipment information received by the medical equipment information reception block is displayed on the display unit.

Since the medical equipment information such as the instruction manual of the medical equipment and so forth need not be annexed in the form of paper to the medical equipment as in the prior art and besides the instruction manual can be managed readily, the medical equipment information can be annexed at a low cost to the medical equipment.

Further, with the configuration described above, if a health care worker who uses the medical equipment opens the packing unit, then the medical equipment information is automatically transmitted to the medical equipment information reception block and displayed on the display unit.

Accordingly, it is possible to allow the health care worker or the like to confirm the instruction manual information and so forth of the medical equipment relating to use of the medical equipment.

Preferably, the medical equipment information management system is configured such that the medical equipment information includes product information for insurance claim paperwork, and the medical equipment information management system further includes an insurance claim document preparation block configured to prepare an insurance claim document based on the product information for insurance claim paperwork.

With the configuration described above, since the medical equipment information management system includes the insurance claim document preparation block, an insurance claim document, which has conventionally been prepared by manual operation, can be prepared automatically. Consequently, laborsaving can be anticipated. Further, since no manual operation is used, also it is possible to prevent an input error or the like.

Preferably, the medical equipment information management system is configured such that the medical equipment information includes instruction manual information, and a contents confirmation screen image for urging a user to carry out contents confirmation is displayed after the instruction manual information is displayed on the display unit; and the insurance claim document preparation block operates only when inputting for contents confirmation is carried out on the content confirmation screen image.

With the configuration described above, it can be decided on the contents conformation screen image whether or not there is a fact of conformation of the instruction manual, whose confirmation by a user such as a health care worker is demanded, by the user. Further, if there is no input for contents confirmation by the user, then the insurance claim document is not prepared. Therefore, the user can carry out the confirmation with a higher degree of certainty.

Preferably, the medical equipment information management system is configured such that the medical equipment information storage medium is disposed at a seal portion for opening of the packing unit.

With the configuration described above, the seal portion for opening of the packing unit is a portion which is broken and opened without fail by the user when the medical equipment information storage medium is to be used. Therefore, if the user opens the seal portion for opening, then the medical equipment information is transmitted to the medical equipment information reception block without fail. Consequently, such a situation that, although the packing unit is opened, the medical equipment information such as the instruction manual is not displayed on the display unit can be prevented.

Preferably, the medical equipment information management system is configured such that the medical equipment information storage medium starts operation in response to an external stimulus thereto to transmit the medical equipment information to the medical equipment information reception block.

Preferably, the medical equipment information management system is configured such that the medical equipment information reception block is placed only at a specific opening place for the packing unit of the medical equipment.

With the configuration described above, in the case of a piece of medical equipment whose packing unit is to be opened at a specified place like a catheter, even if the packing unit is opened at a place other than the specified place for opening, this does not conform to an original method of use and does not make an object of an insurance claim.

In this regard, with the configuration described above, the medical equipment information reception block is provided only at the original place specified for opening but is not provided at any other place. Therefore, even if the packing unit is opened at any other place, the medical equipment information reception block does not receive the medical equipment information from the medical equipment information storage medium.

Accordingly, since an insurance claim document is prepared only by the original method of use, an appropriate insurance claim can be guaranteed.

Preferably, the medical equipment information management system is configured such that the medical equipment information received by the medical equipment information reception block includes medical equipment information by language corresponding to a plurality of languages, and when the display unit displays the medical equipment information, a language selection screen image for selecting medical equipment information by language to be displayed is displayed, and the medical equipment information is displayed with the medical equipment information by language selected on the language selection screen image.

With the configuration described above, medical equipment information of an unnecessary language is not displayed, and therefore, the user can read the medical equipment information readily.

Preferably, the medical equipment information management system is configured such that the medical equipment information received by the medical equipment information reception block includes medical equipment information by language corresponding to a plurality of languages, and the medical equipment information management system further includes a specific by-language medical equipment information storage block configured to store specific medical equipment information by language which is specific medical equipment information by language to be displayed on the display unit, the medical equipment information management system further including a language specification block configured to specify, when the display unit displays the medical equipment information, the medical equipment information by language to be displayed from within the medical equipment information received by the medical equipment information reception block based on the specific medical equipment information by language.

With the configuration described above, since the user himself or herself need not select a language, the operability is improved.

According to the present invention, the object described above is achieved by a control method for medical equipment information management system, including a medical equipment information storage medium capable of storing medical equipment information therein and transmitting the stored medical equipment information and disposed in a packing unit configured to package medical equipment, a medical equipment information reception block configured to receive the medical equipment information transmitted from the medical equipment information storage medium, and a display unit configured to display the medical equipment information received by the medical equipment information reception block, wherein the medical equipment information storage medium cannot transmit the medical equipment information when the packing unit is in a non-opened state, but transmits the medical equipment information if the packing unit is opened.

Advantageous Effects

As described above, with the present invention, the medical equipment information management system and the medical equipment information management method can be provided wherein medical equipment information such as an instruction manual can be appended readily and at a low cost to medical equipment while confirmation or the like of the medical equipment information by a user is assured.

MODE FOR CARRYING OUT THE INVENTION

In the following, preferred embodiments of the present invention are described in detail with reference to the accompanying drawings and so forth.

It is to be noted that, since the embodiments described below are preferred forms in embodying the present invention, unless it is specifically described in the following description that the present invention is limited, the scope of the present invention is not restricted to the embodiments.

First Embodiment

Figure 1:
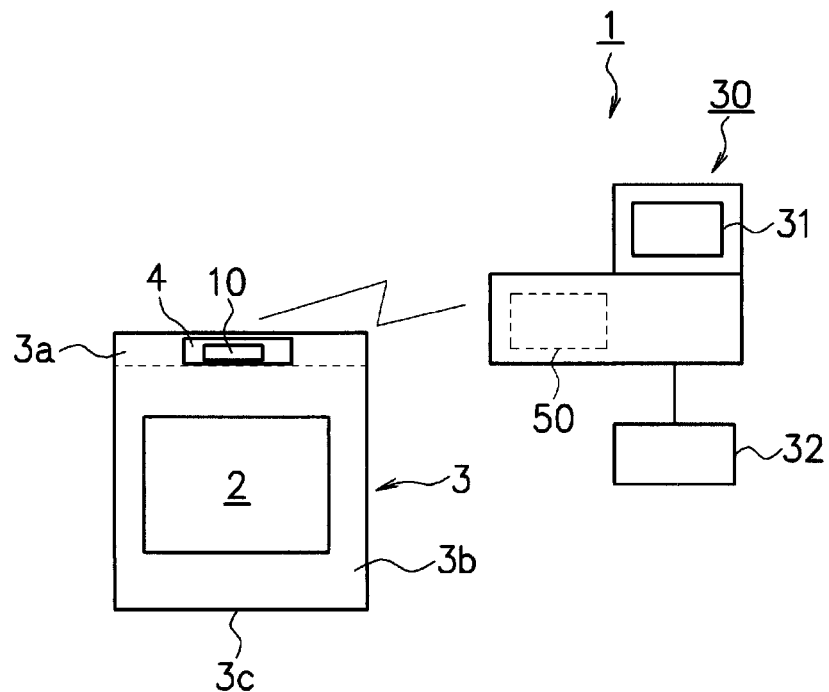
FIG. 1 is a schematic view showing a medical equipment information management system according to a first embodiment of the present invention.

FIG. 1 is a schematic view showing a medical equipment information management system 1 according to a first embodiment of the present invention.

As shown in FIG. 1, the medical equipment information management system 1 has, for example, a catheter 2 which is a piece of medical equipment. This catheter 2 is a hollow flexible pipe used for medical care, and is used such that it is inserted into a lumen region such as a digestive tract or a urinary duct or a blood vessel to carry out drainage of body fluids such as body fluids of thoracic cavity or abdominal cavity or drip infusion of drug solution or contrast agent. In the present embodiment, the catheter 2 is, for example, a stent indwelling catheter for the coronary artery.

Further, since this catheter 2 is a stent indwelling catheter for the coronary artery and is used for a surgical operation, it is accommodated in a sterilized state and in a sealed state, for example, in a packaging bag 3 which is a packing unit.

Accordingly, since the catheter 2 accommodated in the packaging bag 3 is transported or the like in a state in which the sterilized state is maintained, it can be transported or the like in a clean state.

Further, for example, a seal portion 3a which is an opening seal portion is formed on the mouth side of the packaging bag 3 as shown in FIG. 1. This seal portion 3a is a portion for placing the inside of the packaging bag 3 into a sealed state by pasting a front face 3b and a rear face 3c of the packaging bag 3 to each other.

At the seal portion 3a, an IC tag accommodation portion 4 which accommodates, for example, an IC tag 10 which is a medical equipment information storage medium is formed as shown in FIG. 1.

Here, the IC tag 10 is configured such that an IC (Integrated Circuits (integrated circuits)) chip, a small antenna and so forth are embedded in a tag-shaped article and information stored therein is transmitted by radio waves.

Figure 2:
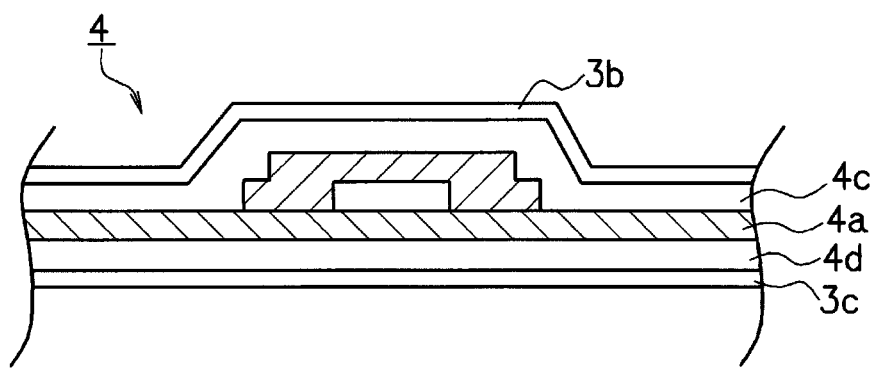
FIG. 2 is a schematic sectional view showing an IC tag accommodation portion and so forth of FIG. 1.

FIG. 2 is a schematic sectional view showing the IC tag accommodation portion 4 and so forth of FIG. 1.

As shown in FIG. 2, the IC tag accommodation portion 4 is disposed in such a manner that it is sandwiched between the front face 3b and the rear face 3c of the packaging bag 3. Further, the IC tag 10 is accommodated in the inside of the IC tag accommodation portion 4.

As shown in FIG. 2, the IC tag accommodation portion 4 has an radio wave shielding layer 4a disposed in such a manner as to surround the IC tag 10 and has a plastic layer 4c formed on the front face 3b side of the radio wave shielding layer 4a in such a manner as to cover the radio wave shielding layer 4a.

Further, a mount 4d is disposed on the rear face 3c side of the radio wave shielding layer 4a in such a manner as to cover the radio wave shielding layer 4a.

This radio wave shielding layer 4a is formed from a metal thin film of aluminum or the like. Since the IC tag 10 is covered with the radio wave shielding layer 4a, plastic layer 4c and mount 4d in this manner, it cannot receive radio waves from the outside.

However, if a health care worker or the like who is a user of the catheter 2 breaks the seal of the seal portion 3a to place the packaging bag 3 into an open state in order to use the catheter 2 in the packaging bag 3, then the front face 3b and the rear face 3c of the packaging bag 3 shown in FIG. 1 are separated from each other, and also the IC tag accommodation portion 4 is separated.

Figure 3:
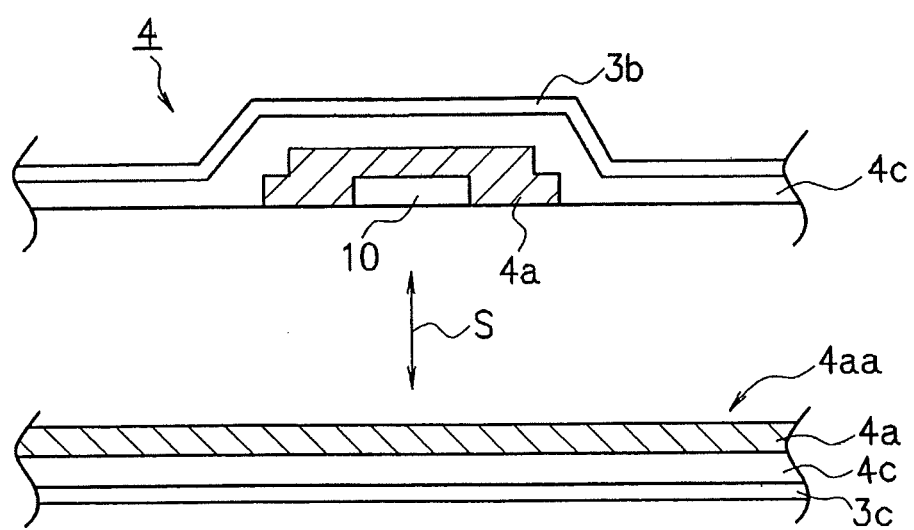
FIG. 3 is a schematic view showing a separation state of the IC tag accommodation portion and so forth of FIG. 1.

FIG. 3 is a schematic view illustrated a separated state of the IC tag accommodation portion 4 and so forth shown in FIG. 1.

As shown in FIG. 3, the radio wave shielding layer 4a of the IC tag accommodation portion 4 has a separation portion 4aa at which the rear face 3c and the front face 3b are separated from each other, and the IC tag accommodation portion 4 is divided into the two portions across the separation portion 4aa as indicated by an arrow mark S in FIG. 3.

Consequently, the IC tag 10 accommodated in the IC tag accommodation portion 4 is placed into an open state, in which it can receive radio waves from the outside.

Incidentally, as shown in FIG. 1, the medical equipment information management system 1 has a management apparatus 30. The management apparatus 30 has, for example, a tag information reader 50 which is a medical equipment information reception block which carries out communication with the IC tag 10 to acquire medical equipment information of a catheter or the like.

In particular, the management apparatus 30 is configured such that, if radio waves are transmitted from the tag information reader 50 and received by the IC tag 10 in the IC tag accommodation portion which is in the state illustrated in FIG. 3, then communication is started. Information and so forth to be transmitted are hereinafter described.

Further, as shown in FIG. 1, the management apparatus 30 has a display unit 31 serving as a displaying block, a printer 32 serving as a printing apparatus of data, and so forth.

The management apparatus 30 and so forth of FIG. 1 have a computer and so forth. This computer has a CPU (Central Processing Unit), a RAM (Random Access Memory), a ROM (Read Only Memory) and so forth and is disposed, for example, through a bus or the like.

This bus is an internal bus which has a function of connecting all devices to each other and has an address bus and/or a data bus. The CPU carries out processing of a predetermined program and controls the ROM and so forth connected to the bus. The ROM has various programs, various kinds of information and so forth stored therein. The RAM has a function as an area for contrasting the contents of the memory during processing of a program and executing a program.

Figure 4:
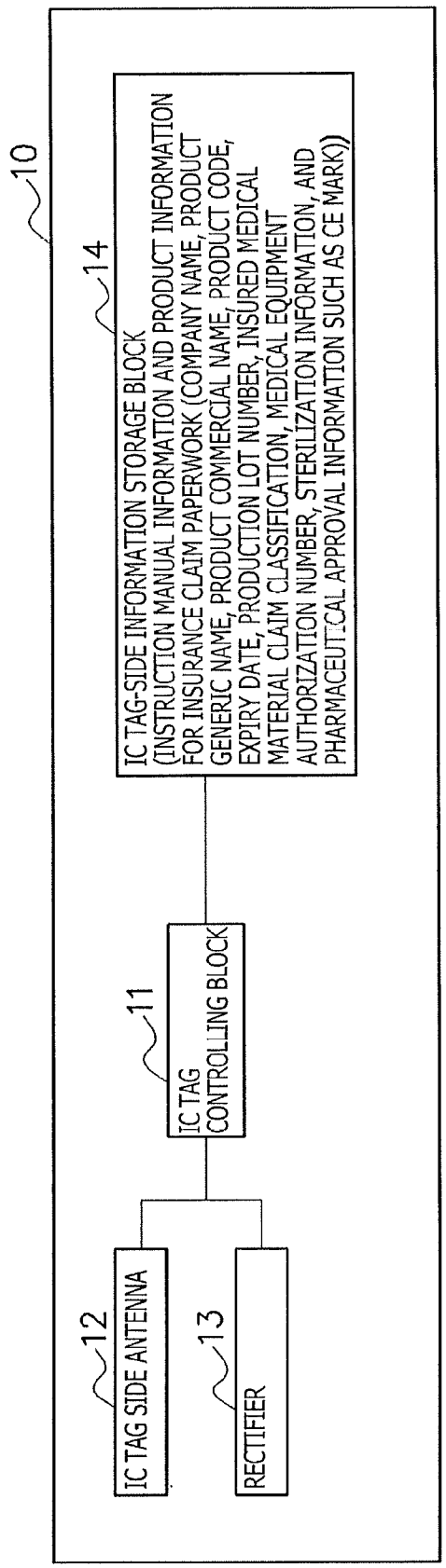
FIG. 4 is a schematic block diagram showing a principal configuration of an IC tag.

FIG. 4 is a schematic block diagram showing principal components of the IC tag 10.

As shown in FIG. 4, the IC tag 10 has an IC tag controlling block 11 and further has an IC tag side antenna 12 and a rectifier 13 for communication. The IC tag side antenna 12 and the rectifier 13 are controlled by the IC tag controlling block 11.

The IC tag 10 further has an IC tag side information storage block 14, in which, for example, instruction manual information and product information for insurance claim paperwork which are medical equipment information of a piece of medical equipment such as the catheter 2 is stored.

The instruction manual information is various kinds of information for using the catheter 2 and so forth and is described in a large number of languages such as Japanese, English, French and Chinese.

The instruction manual information in the languages is an example of by-language medical equipment information.

Accordingly, the catheter 2 accommodated in the packaging bag 3 is configured such that, when it is used not only in Japan but also in foreign countries, a health care worker of the country can read the instruction manual in the language of the country.

Further, the product information for insurance claim paperwork stored in the IC tag side information storage block 14 is information for allowing, when the catheter 2 is used to carry out a surgical operation or the like in a hospital or the like, the hospital to claim a score of a health insurance and so forth.

In particular, the product information for insurance claim paperwork includes a company name, a product generic name, a product commercial name, a product code, an expiry date, a production lot number, an insured medical material claim classification, a medical equipment authorization number, sterilization information, pharmaceutical approval information such as the CE mark (safety mark in Europe), and so forth.

Figure 5:
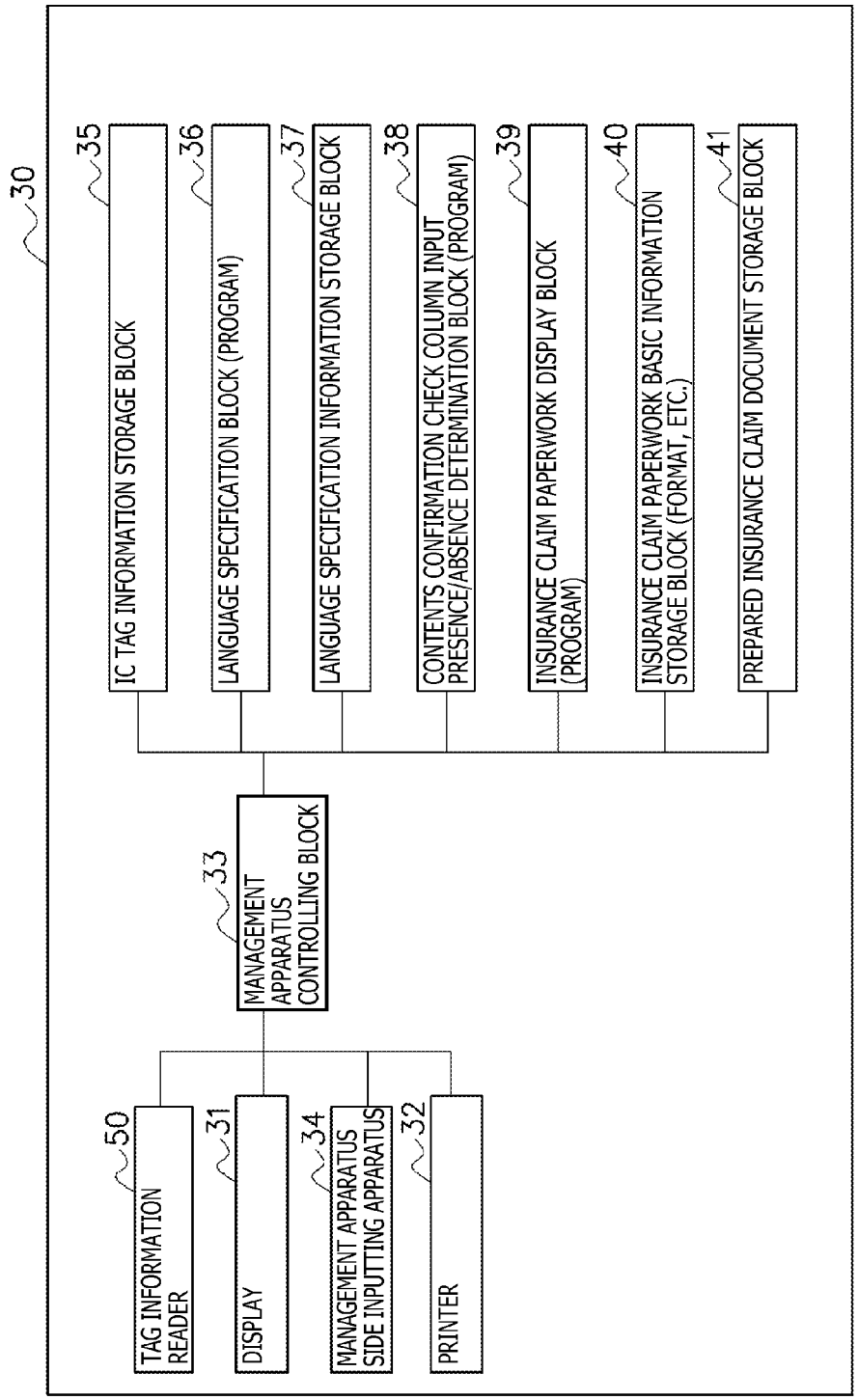
FIG. 5 is a schematic block diagram showing a principal configuration of a management apparatus of FIG. 1.

FIG. 5 is a schematic block diagram showing principal components of the management apparatus 30 of FIG. 1.

As shown in FIG. 5, the management apparatus 30 has a management apparatus controlling block 33 and further has the tag information reader 50, the display unit 31, the printer 32 and a management apparatus side inputting apparatus 34 for inputting various kinds of information. The tag information reader 50, display unit 31, printer 32 and management apparatus side inputting apparatus 34 are controlled by the management apparatus controlling block 33.

Further, while the management apparatus 30 includes various storage blocks, programs and so forth as shown in FIG. 5, they are hereinafter described.

Figure 6:
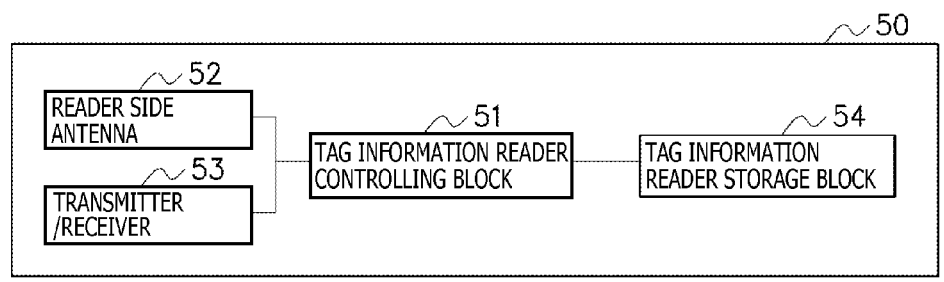
FIG. 6 is a schematic block diagram showing a principal configuration of a tag information reader of FIGS. 1 and 5.

FIG. 6 is a schematic block diagram showing principal components of the tag information reader 50 of FIGS. 1 and 5.

As shown in FIG. 6, the tag information reader 50 has a tag information reader controlling block 51, and further has a reader side antenna 52 and a transmitter/receiver 53 for communicating with the IC tag 10. The reader side antenna 52 and the transmitter/receiver 53 are controlled by the tag information reader controlling block 51.

The tag information reader 50 has a tag information reader storage block 54 for temporarily storing received information and so forth as occasion demands as well.

Figure 7:
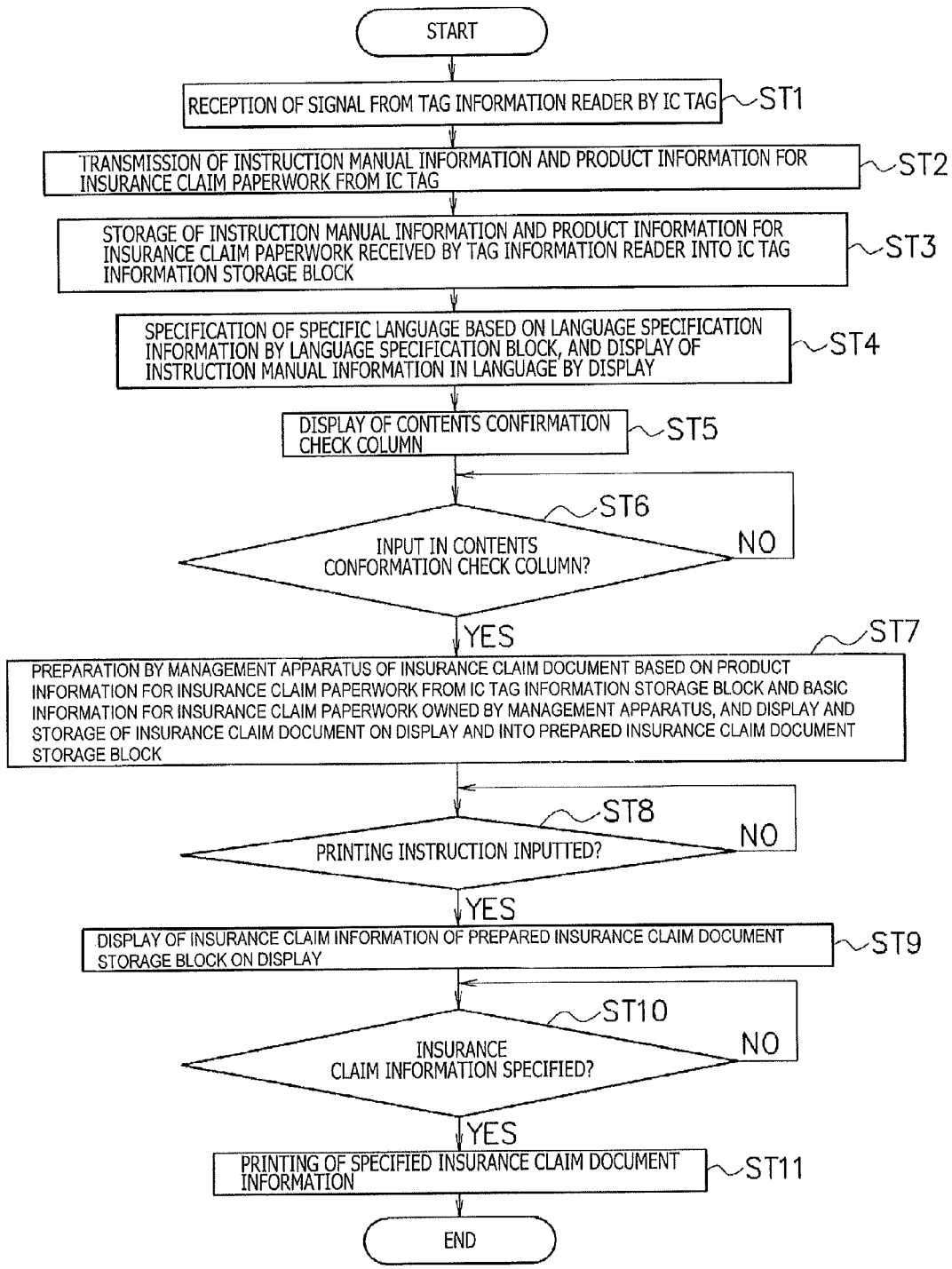
FIG. 7 is a schematic flow chart illustrating principal operation and so forth of the medical equipment information management system according to the embodiment.

FIG. 7 is a schematic flow chart illustrating principal operation and so forth of the medical equipment information management system 1 according to the present embodiment.

In the following, operation and so forth of the medical equipment information management system 1 are described with reference to the flow chart of FIG. 7 and also the components and so forth in FIGS. 1 to 6 are described together.

In the following, description is given of an example wherein a packaging bag 3 which is stored in a hospital or the like in a state in which a catheter 2 is accommodated therein is opened in order to actually use the catheter 2 in an operation room or the like and, for example, a health care worker who is a user confirms the instruction manual to prepare an insurance claim document.

First, the health care worker who is to use the catheter 2 prepares the catheter 2 shown in FIG. 1 accommodated in the packaging bag 3.

Then, if the health care worker breaks the seal portion 3a of FIG. 1 as described hereinabove, then the front face 3b and the rear face 3c of the packaging bag 3 are separated from each other as shown in FIG. 3, and the seal of the seal portion 3a is broken and the mouth side of the packaging bag 3 is placed into an open state.

Consequently, the IC tag accommodation portion 4 is separated from the separation portion 4aa of FIG. 3 and also the IC tag 10 accommodated in the inside of the radio wave shielding layer 4a is placed into an open state and permitted to receive radio waves from the tag information reader 50 of FIG. 1.

In this state, the processing advances to step ST1 of FIG. 7.

At step ST1, the IC tag 10 receives radio waves from the tag information reader 50 of the management apparatus 30 of FIG. 1.

Then, the processing advances to step ST2, at which the IC tag 10 transmits instruction manual information and product information for insurance claim paperwork stored in the IC tag side information storage block 14 of FIG. 4 to the tag information reader 50 of FIG. 1 through the IC tag side antenna 12 and so forth.

Thereafter, the processing advances to step ST3. At step ST3, the instruction manual information and so forth received by the tag information reader 50 are stored into an IC tag information storage block 35 of FIG. 5 through the tag information reader storage block 54 of FIG. 6 as occasion demands.

Then, the processing advances to step ST4. The step ST4 is a step at which the "instruction manual information"

acquired from the IC tag 10 is displayed on the display unit 31 of the management apparatus 30.

The instruction manual information stored into the IC tag information storage block 35 at step ST3 represents information stored in a plurality of languages of different countries as described hereinabove. Therefore, if all of the instruction manual information of the plural languages is displayed on the display unit 31, then this is cumbersome to the user such as a health care worker.

Therefore, in the present embodiment, a language specification block (program) 36 of FIG. 5 operates at step ST4 to refer to a language specification information storage block 37 which is a specific by-language medical equipment information storage block to acquire information of a specific language, for example, the Japanese language. Then, the language specification block (program) 36 acquires the instruction manual information of the Japanese language from the IC tag information storage block 35 and displays the instruction manual information on the display unit 31.

In this language specification information storage block 37, language information of the country in which the hospital or the like is located (for example, the Japanese language or the like) is stored in advance.

Since the instruction manual of the catheter 2 is displayed on the display unit 31 in this manner, the health care worker who uses the catheter 2 can confirm the "instruction manual."

Further, since, in the present embodiment, the instruction manual is not annexed to the catheter 2 but is stored in the IC tag 10, management of the instruction manual is easy and besides the cost can be reduced.

Particularly, since the instruction manual of each of the languages of the large number of countries is not in the form of paper, the management is facilitated significantly.

Furthermore, in the present embodiment, since "instruction manual information" is automatically displayed on the display unit 31 only if a health care worker breaks the seal portion 3a of the packaging bag 3, the health care worker who is a user of the catheter 2 does not miss the confirmation of the "instruction manual."

Further, since the IC tag accommodation portion 4 is formed on the seal portion 3a, occurrence of such a situation that, although the packaging bag 3 is opened, the medical equipment information such as the instruction manual is not displayed on the display unit 31 can be prevented.

Incidentally, a configuration different from that of the present embodiment may be used. In particular, according to the different configuration, at this step, a language selection screen image for displaying the language type information (for example, Japanese, English, French, Chinese and so forth) in the IC tag information storage block 35 on the display unit 31 is presented, and then a health care worker is caused to select a language every time on the display unit 31. Thereafter, the "instruction manual information" of the selected language is displayed on the display unit 31.

Another configuration different from that of the present embodiment may be adopted. In particular, according to the different configuration, the management apparatus 30 has a GPS (global positioning system) apparatus and measures the altitude and the latitude of the position of the management apparatus 30 itself, and the name of the country of the management apparatus 30 is grasped from the altitude and latitude and map information owned by the management apparatus 30. In this instance, the management apparatus 30 further includes country name corresponding language information and therefore can specify the language of the country from the country name.

Further, a configuration may be adopted wherein the "instruction manual information" of the language specified in this manner is displayed on the display unit 31.

After the "instruction manual information" is displayed on the display unit 31 at step ST4, the processing advances to step ST5. At step ST5, a contents confirmation screen image is displayed to the health care worker who is the user.

Then, the health care worker would read the "instruction manual information" displayed on the display unit 31 of the management apparatus 30 and then operate the management apparatus side inputting apparatus 34 (for example, a keyboard or the like) of FIG. 5 to place a check mark into a "contents confirmation check column" on the display unit 31.

Consequently, in the present embodiment, upon use of the catheter 2, confirmation of the "instruction manual" by the health care worker can be made surer.

Thereafter, the processing advances to step ST6. At step ST6, a contents confirmation check column input presence/absence determination block (program) 38 of FIG. 5 operates to decide whether or not a check mark is inputted into the "content confirmation check column" at step ST5 from the health care worker.

Then, if it is confirmed that a check mark is placed in the "contents confirmation check column," then the processing advances to step ST7 and so forth at which preparation of an insurance claim document of a health insurance is carried out and so forth.

In this manner, in the present embodiment, if a health care worker or the like who is a user does not confirm the "instruction manual" of the catheter 2, then the processing cannot advance to an insurance claim paperwork and so forth. Accordingly, the medical equipment information management system 1 of the present embodiment is configured such that contents confirmation of the "instruction manual" by the health care worker or the like is carried out with a higher degree of certainty.

At step ST7, for example, an insurance claim paperwork display block (program) 39 which is an insurance claim preparation block of the management apparatus 30 operates to acquire the "product information for insurance claim paperwork" stored in the IC tag information storage block 35 and automatically prepares an insurance claim of a health insurance based on information of a format and so forth stored in an insurance claim paperwork basic information storage block 40 of FIG. 5.

Consequently, an insurance claim document which has conventionally been prepared by manual operation by a health care worker or the like can be prepared automatically, and laborsaving can be anticipated. Further, in the present embodiment, since product information for insurance claim paperwork such as a company name is not carried out by manual inputting, occurrence of an input error can be prevented.

Further, the data of the prepared insurance claim document at step ST7 is stored into and retained in a prepared insurance claim document storage block 41 of FIG. 5.

Then, the processing advances to step ST8. At step ST8, it is decided whether or not a printing instruction of the insurance claim document is issued to the printer 32, and if a printing instruction is issued, then the processing advances to step ST9.

At step ST9, a table of contents of the data in the prepared insurance claim document storage block 41 is displayed on the display unit 31.

Then at step ST10, it is decided whether or not data to be printed is specified from the table of contents and so forth on the display unit 31 through the management apparatus side inputting apparatus 34 by the health care worker. If data to be printed is specified, then a desired insurance claim document can be obtained in the form of paper at step ST11.

First Modification to the First Embodiment

In the first embodiment described above, as shown in FIG. 1, the IC tag 10 is configured such that it receives radio waves from the tag information reader 50 and then transmits information in the IC tag 10 to the tag information reader 50 side. However, in the present invention, such an IC tag 110 and an IC tag accommodation portion 140 according to a first modification as described below may be used.

Figure 8:
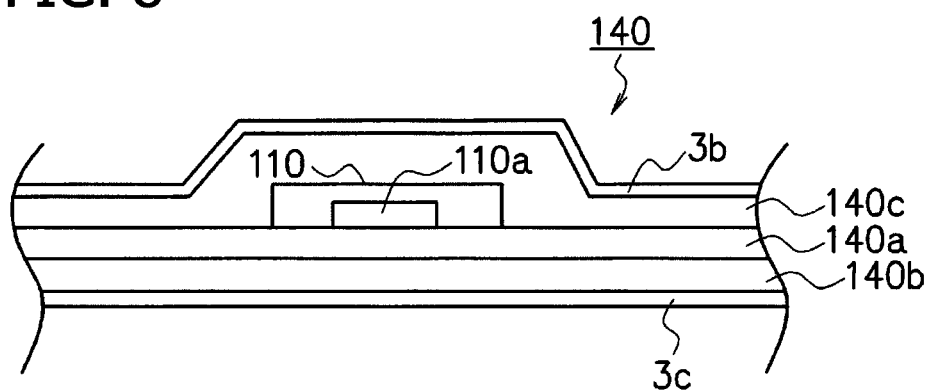
FIG. 8 is a schematic sectional view showing an IC tag accommodation portion according to a first modification to the first embodiment.
Figure 9:
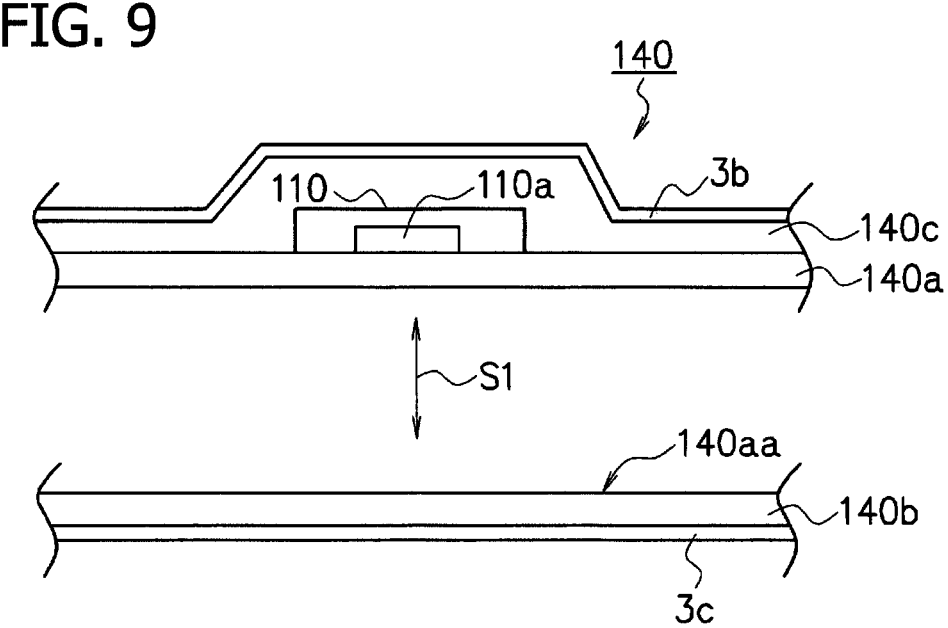
FIG. 9 is another schematic sectional view showing the IC tag accommodation portion according to the first modification to the first embodiment.

FIGS. 8 and 9 are schematic sectional views showing the IC tag accommodation portion 140 according to the first modification to the first embodiment.

Since the IC tag accommodation portion 140 according to the present modification has a configuration common to that of the IC tag accommodation portion 4 according to the first embodiment described hereinabove, common components are denoted by like reference symbols or the like and description of them is omitted herein. In the following, description is given principally of differences.

As shown in FIG. 8, a plastic layer 140c is formed on the front face 3b side of the IC tag 110 in the present modification.

Further, the IC tag 110 has a light receiving portion 110a on the rear face 3c side thereof (lower side in FIG. 8).

Further, on the side of the IC tag 110 on which the light receiving portion 110a is formed, a transparent or opaque plastic film 140a is formed in such a manner as to contact with the light receiving portion 110a and the IC tag 110.

Furthermore, on the plastic film 140a on the rear face 3c side, a light blocking layer 140b formed from an opaque film containing light blocking paint such as black paint or the like in place of the radio wave shielding layer 4a of FIGS. 2 and 3 of the first embodiment is formed.

Accordingly, the IC tag 110 is configured such that, when a health care worker or the like opens the packaging bag 3 and the IC tag accommodation portion 140 is separated at a separation portion 140aa as indicated by an arrow mark S1 as shown in FIG. 9, for example, light which is an external stimulus enters the light receiving portion 110a of FIG. 9 from the outside and the light receiving portion 110a detects this light, whereby a circuit is established in the IC tag 110 to issue a signal.

Accordingly, if the IC tag accommodation portion 140 is separated as shown in FIG. 9, then the IC tag 110 of the present modification receives an external stimulus of light and establishes a circuit therein, and the instruction manual information, the product information for insurance claim paperwork and so forth in the IC tag 110 in the present modification are transmitted to the tag information reader 50 of FIG. 1.

Further, while, in the present modification, the IC tag accommodation portion 140 is configured such that it is formed in the packaging bag 3, the IC tag accommodation portion 140 is not limited to this but may be configured in such a structure that it can be additionally provided to a packaging bag and is attached or pasted to an existing packaging bag.

Second Modification to the First Embodiment

Figure 10:
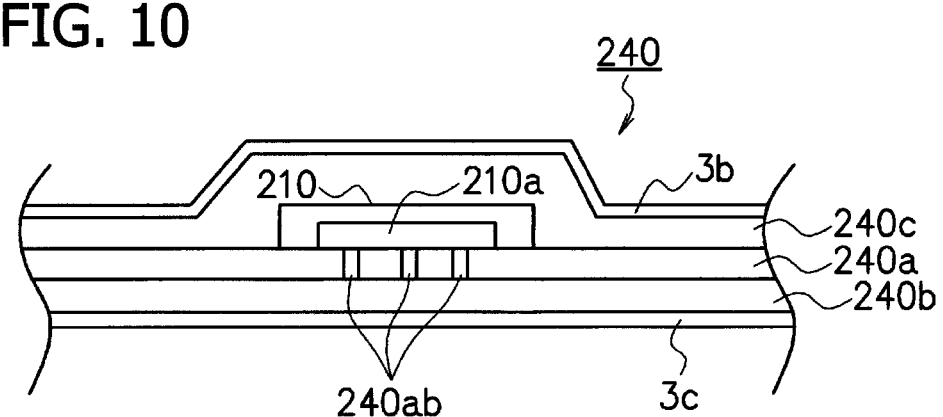
FIG. 10 is a schematic sectional view showing an IC tag accommodation portion according to a second modification to the first embodiment.
Figure 11:
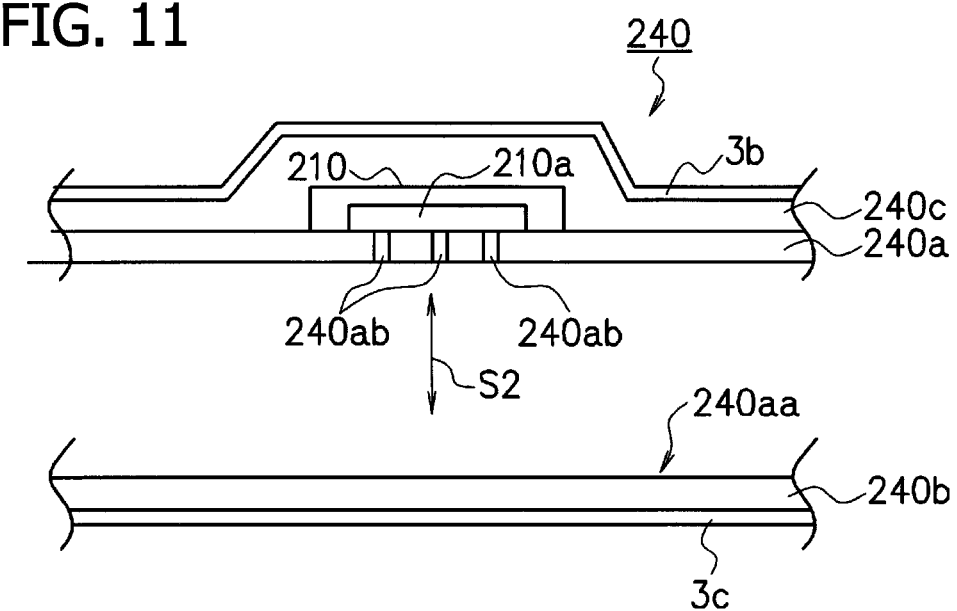
FIG. 11 is another schematic sectional view showing the IC tag accommodation portion according to the second modification to the first embodiment.

FIGS. 10 and 11 are schematic sectional views showing an IC tag accommodation portion 240 according to a second modification to the first embodiment. The IC tag accommodation portion 240 according to the present modification has a configuration common to that of the IC tag accommodation portions 4 and 140 according to the first embodiment and so forth described hereinabove. Therefore, such common components are denoted by like reference symbols or the like and description of them is omitted. Thus, the following description is given principally of differences.

As shown in FIG. 10, a plastic layer 240c is formed on the front face 3b side of an IC tag 210 according to the present modification.

Further, the IC tag 210 has a sensor 210a, which reacts with air or water, on the rear face 3c side thereof (lower side in FIG. 10).

Further, on the side of the IC tag 210 on which the sensor 210a is formed, a plastic film 240a is formed in such a manner as to contact with the sensor 210a and the IC tag 210.

Further, on the rear face 3c side of the plastic film 240a, an air and water blocking layer 240b which blocks air, water and so forth is formed in place of the radio wave shielding layer 4a of FIGS. 2 and 3 in the first embodiment.

Further, in the plastic film 240a of FIG. 10, a plurality of through-holes 240ab which couple the air and water blocking layer 240b disposed on the rear face 3c side and the sensor 210a to each other are formed.

The through-holes 240ab are in a closed up state when the plastic film 240a is covered with the air and water blocking layer 240b as shown in FIG. 10, and air or water from the outside does not reach the sensor 210a through the through-holes 240ab.

However, if a health care worker or the like opens the packaging bag 3 and the IC tag accommodation portion 240 is separated at a separation portion 240aa as indicated by an arrow mark S2 as shown in FIG. 11, then, for example, air or water which is an external stimulus enters the sensor 210a from the outside through the through-holes 240ab of FIG. 11. Thus, the sensor 210a detects this air or water and a circuit is established in the IC tag 210 to issue a signal.

Accordingly, if the IC tag accommodation portion 240 is separated as shown in FIG. 11, then the IC tag 210 of the present modification receives an external stimulus such as air or water and establishes a circuit therein. Consequently, the instruction manual information, product information for insurance claim paperwork and so forth in the IC tag 210 of the present modification are transmitted to the tag information reader 50 of FIG. 1.

Further, while, in the present modification, the IC tag accommodation portion 240 is formed in the packaging bag 3, the IC tag accommodation portion 240 is not limited to this but may be configured in such a structure that it can be additionally provided to a packaging bag and is attached or pasted to an existing packaging bag.

Third Modification to the First Embodiment

Figure 12:
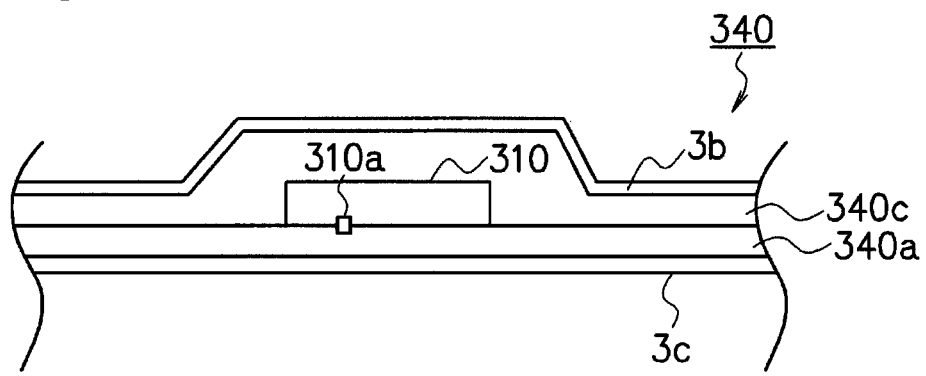
FIG. 12 is a schematic sectional view showing an IC tag accommodation portion according to a third modification to the first embodiment.
Figure 13:
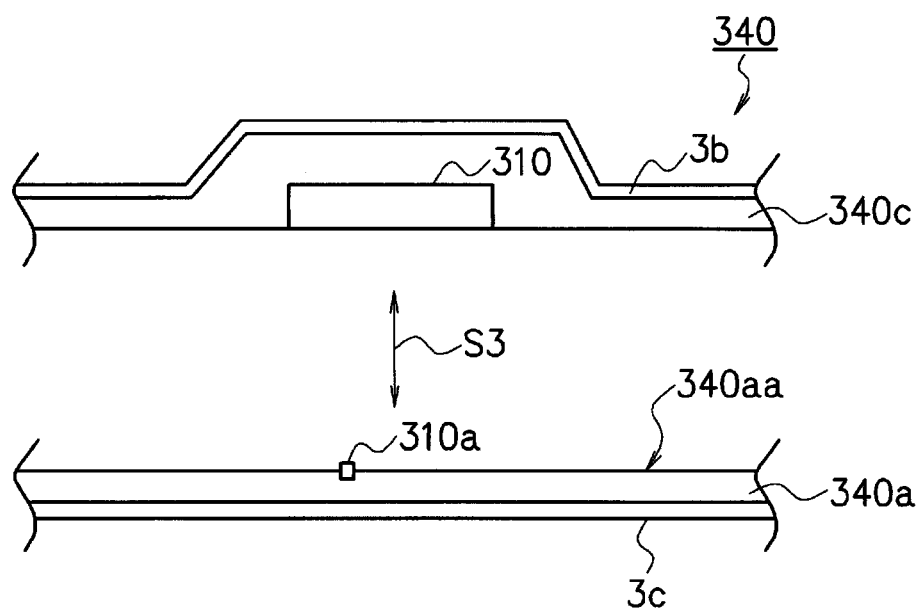
FIG. 13 is another schematic sectional view showing the IC tag accommodation portion according to the third modification to the first embodiment.

FIGS. 12 and 13 are schematic sectional views showing an IC tag accommodation portion 340 according to a third modification to the first embodiment. The IC tag accommodation portion 340 has a configuration common to the IC tag accommodation portions 4, 140 and 240 according to the first embodiment and so forth described hereinabove, and therefore, common components are denoted by like reference symbols or the like and description of them is omitted. Thus, description is given below principally of differences.

As shown in FIG. 12, a plastic layer 340c is formed on the front face 3b side of an IC tag 310 according to the present modification.

Further, a plastic film 340a is disposed on the rear face 3c side of the IC tag 310 (lower side in FIG. 12).

Further, an obstacle 310a is disposed between the IC tag 310 and the plastic film 340a such that it extends across them.

The obstacle 310 is configured such that it is disposed so as to project into the IC tag 310 in a state in which it is fixed to the plastic film 340a.

Further, the obstacle 310a is configured such that, if it is disposed in the IC tag 310, then it cuts the circuit in the IC tag 310 so as not to establish a circuit.

Further, the rear face 3c is disposed on the plastic film 340a.

Thus, when a health care worker or the like opens the packaging bag 3 and the IC tag accommodation portion 340 is separated at a separation portion 340aa as indicated by an arrow mark S3 as shown in FIG. 13, if the plastic film 340a is spaced away from the IC tag 310, then also the obstacle 310a fixed to the plastic film 340a is spaced away from the IC tag 310, and a circuit is established in the inside of the IC tag 310 and issues a signal.

Accordingly, if the IC tag accommodation portion 340 is separated as shown in FIG. 13, the IC tag 310 of the present modification establishes a circuit therein to transmit the instruction manual information, the product information for insurance claim paperwork and so forth to the tag information reader 50 of FIG. 1.

Further, while, in the present modification, the IC tag accommodation portion 340 is configured such that it is formed in the packaging bag 3, the IC tag accommodation portion 340 is not limited to this but may be configured in such a structure that it can be additionally provided to a packaging bag and is attached or pasted to an existing packaging bag.

Fourth Modification to the First Embodiment

Figure 14:
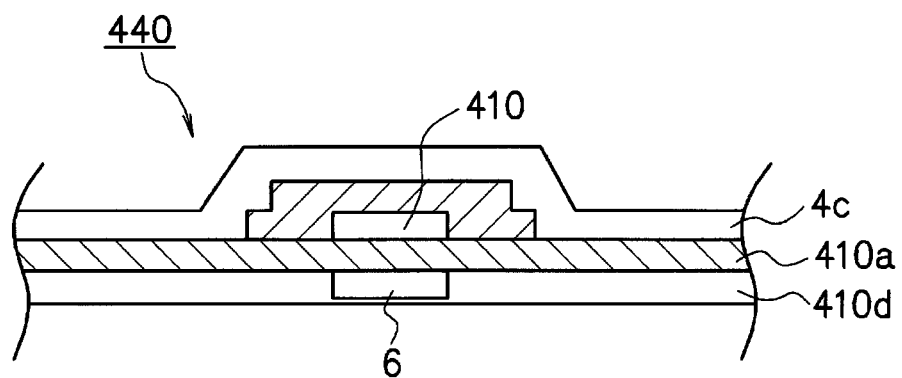
FIG. 14 is a schematic sectional view showing a fourth modification to the first embodiment described above.
Figure 15:
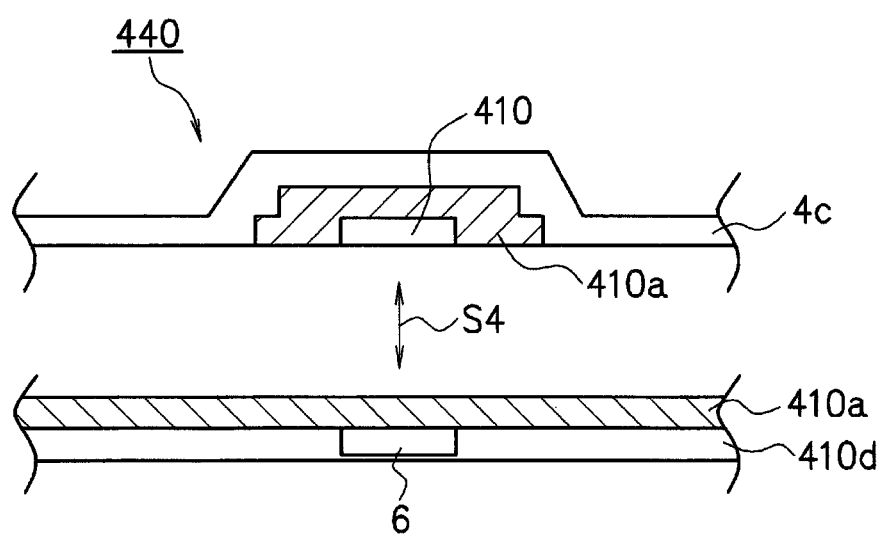
FIG. 15 is another schematic sectional view showing a fourth modification to the first embodiment described above.

FIGS. 14 and 15 are schematic sectional views showing a fourth modification to the first embodiment described hereinabove.

As shown in FIG. 14 and so forth, in the present modification, a magnet 6 is formed on a mount 410d. This magnet 6 is disposed in such a manner as to oppose to an IC tag 410 covered with a blocking layer 410a formed from a metal thin film of aluminum or the like.

In particular, in a state in which an IC tag accommodation portion 440 is not separated as shown in FIG. 14, the IC tag 410 is disposed adjacent the magnet 6 of the mount 410d with the blocking layer 410a interposed therebetween.

Accordingly, the IC tag 410 is in a state in which it is influenced strongly by the magnetic force of the magnet 6.

Meanwhile, in FIG. 15, the IC tag accommodation portion 440 is separated as indicated by an arrow mark S4, and therefore, the IC tag 410 is in a state in which it is less likely to be influenced by the magnet 6.

Further, the IC tag 410 according to the present modification is configured such that, while it is influenced by the magnetic force of the magnet 6, a circuit is not established, but if the influence of the magnetic force of the magnet 6 decreases, then a circuit is established in the IC tag 410 and transmission of information is started.

Accordingly, in the state of FIG. 14, a circuit is not established, and medical equipment information such as instruction manual information and so forth in the IC tag 410 is not transmitted. However, if the IC tag accommodation portion 440 is separated as shown in FIG. 15, then the influence of the magnetic force of the magnet 6 decreases. Therefore, a circuit is established and the medical equipment information is transmitted.

Figure 16:
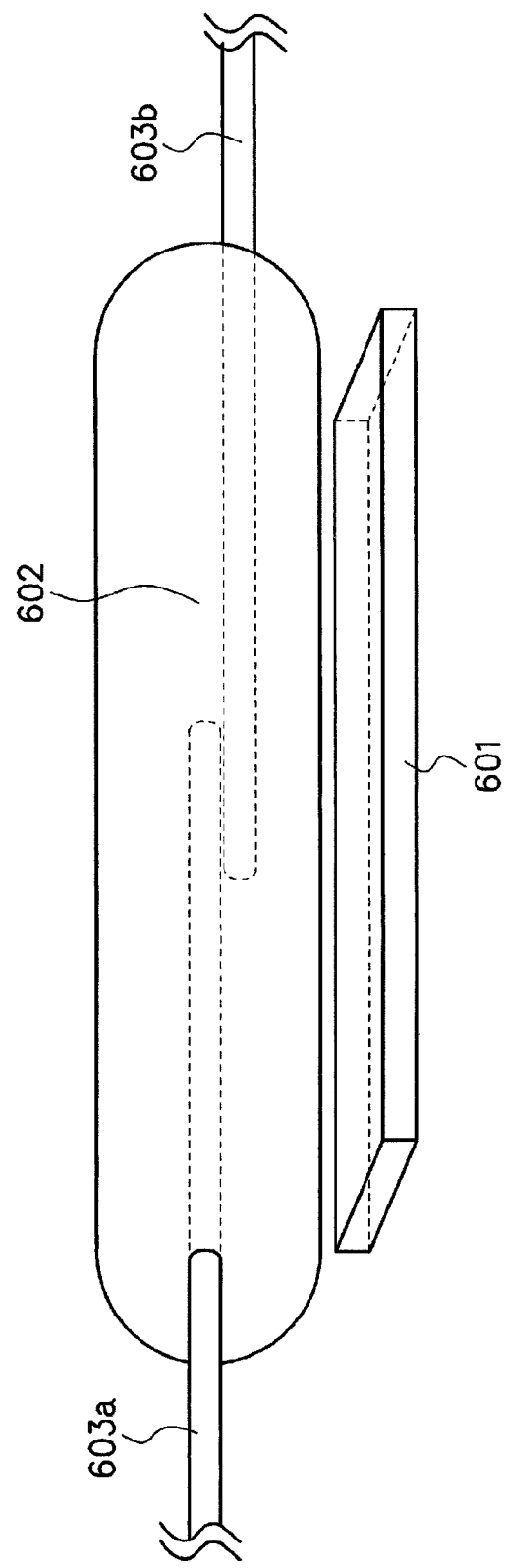
FIG. 16 is a schematic view showing a reed switch in an electric circuit.

This is because a reed switch is provided in the electric circuit of the IC tag 410, and interruption of the electric circuit is described with reference to FIG. 16. FIG. 16 is a schematic view showing the reed switch in the electric circuit.

In the reed switch 600, two magnetic reeds 603a and 603b are overlapped in a predetermined spaced relationship from each other in the proximity of the substantial center of a glass pipe 602 to configure a contact portion. The reed switch 600 is a normally closed type reed switch wherein the contact portion is closed by magnetic attractive force when magnetic fluxes flow from a permanent magnet 601, which serves as a magnetic flux source, to the magnetic reeds 603a and 603b.

In particular, in a state in which the IC tag accommodation portion 410 is not separated, in the IC tag 410, magnetic fluxes from the permanent magnet 601 of the magnetic switch are canceled by magnetic fluxes from the magnet 6 for cancellation, and the contact of the reed switch 600 is opened. Consequently, the electric circuit and the IC tag controlling block 11 are electrically disconnected from each other and the power supply to the IC tag 410 can be turned OFF (power consumption can be reduced to zero). Consequently, even if the storage period in a warehouse or a hospital becomes long, since unnecessary power consumption is not involved, the function of the present invention can be exhibited regardless of storage for a long period of time.

Further, the shape of the permanent magnet 601 and the magnet 6 may not be a square shape or a rectangular shape or may be a circular shape only if they function to interrupt an electric circuit. The permanent magnet 601 may be disposed in such a manner as to cylindrically surround the magnetic reeds.

Further, while, in the present modification, the IC tag accommodation portion 440 is configured such that it is formed in the packaging bag 3, the IC tag accommodation portion 440 is not limited to this but may be configured in such a structure that it can be additionally provided to a packaging bag and is attached or pasted to an existing packaging bag.

Second Embodiment

Figure 17:
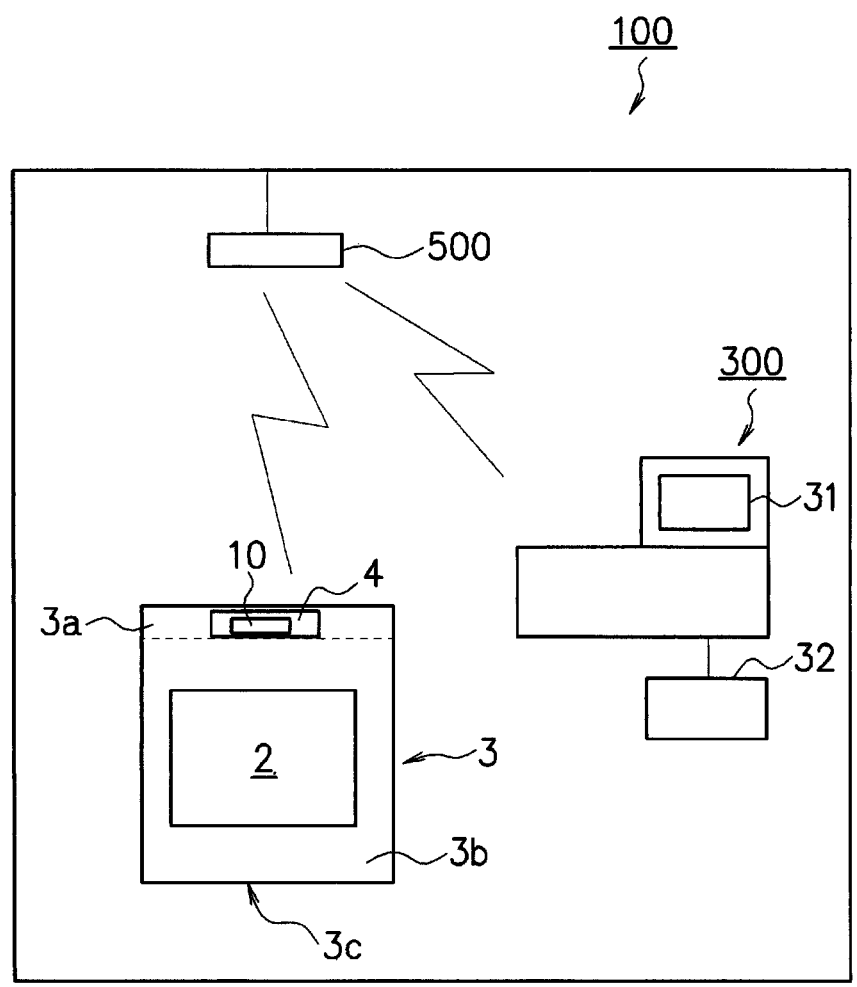
FIG. 17 is a schematic view showing a medical equipment information management system according to a second embodiment of the present invention.

FIG. 17 is a schematic view showing a medical equipment information management system 100 according to a second embodiment of the present invention.

Most of components according to the present embodiment are similar to those of the first embodiment described hereinabove, and therefore, similar components are denoted by like reference symbols or the like. Thus, description is given below principally of differences.

The medical equipment information management system 100 according to the present embodiment is different from the first embodiment described hereinabove in that a tag information reader 500 is not disposed in a management apparatus 300.

Further, the tag information reader 500 is provided fixedly at a specific opening place at which, in the case of a medical device such as, for example, a catheter 2, the packaging bag 3 of the catheter is opened in an operation room, an operation preparation room or the like.

Accordingly, in the case of the catheter 2, even if the packaging bag 3 is opened at a place other than such a specific opening place (operation room or the like), the tag information reader 500 does not receive "product information for insurance claim paperwork" in the IC tag 10. Therefore, upon use of the catheter 2, an insurance claim document is not prepared, and consequently, an appropriate insurance claim of a health insurance can be guaranteed.

On the other hand, if the tag information reader 500 in FIG. 17 receives "instruction manual information" or "product information for insurance claim paperwork" in the IC tag 10, then the information is transmitted to the management apparatus 300 side. The management apparatus 300 receives such information by a management apparatus side communication apparatus (not shown) thereof and stores the information into the IC tag information storage block 35 of FIG. 5.

The present invention is not limited to the embodiments described above. For example, an IC tag may be provided on a cardboard box or a packaging material in which a plurality of commodity products such as syringes are accommodated. Further, since the medical equipment is frequently stored and managed for a long period of time in a warehouse in logistics or in a supplies section in a hospital, it is possible, for example, by providing power supply and storage means in an IC tag and providing a function capable of storing periodical measurement values from a humidity sensor or a temperature sensor in the IC tag, to grasp a storage environment in regard to under what humidity or temperature environment the IC tag has been stored at the same time with opening. Consequently, a medical malpractice or the like which is caused by deterioration of medical equipment because of an unfavorable storage state can be prevented from occurring. Further, while, in the present embodiment, the display unit 31 is adopted for the display unit, the display unit is not limited to this, but, for example, a display apparatus of a palm size which includes the tag information reader 500 and the management apparatus 300 or a display apparatus of a notebook shape of an A4 size may be used.

EXPLANATION OF REFERENCE SYMBOLS 1, 100 . . . Medical equipment information management system, 2 . . . Catheter, 3 . . . Packaging bag, 3a . . . Seal portion, 3b . . . Front face, 3c . . . Rear face, 4, 140, 240, 340, 440 . . . IC tag accommodation portion, 4a . . . Radio wave shielding layer, 4aa, 140aa, 240aa, 340aa . . . Separation portion, 4c, 140c, 240c, 340c . . . Plastic layer, 4d, 410d . . . Mount, 6 . . . Magnet, 10, 110, 210, 310, 410 . . . IC tag, 11 . . . IC tag controlling block, 12 . . . IC tag side antenna, 13 . . . Rectifier, 14 . . . IC tag side information storage block, 30, 300 . . . Management apparatus, 31 . . . Display unit, 32 . . . Printer, 33 . . . Management apparatus controlling block, 34 . . . Management apparatus side inputting apparatus, 35 . . . IC tag information storage block, 36 . . . Language specification block (program), 37 . . . Language specification information storage block, 38 . . . Contents confirmation check column input presence/absence determination block (program), 39 . . . Insurance claim paperwork display block (program), 40 . . . Insurance claim paperwork basic information storage block, 41 . . . Prepared insurance claim document storage block, 50, 500 . . . Tag information reader, 51 . . . Tag information reader controlling block, 52 . . . Reader side antenna, 53 . . . Transmitter/receiver, 54 . . . Tag information reader storage block, 110a . . . Light receiving portion, 140a, 240a, 340a . . . Plastic film, 140b . . . Light blocking layer, 210a . . . Sensor, 240b . . . Air and water blocking layer, 240ab . . . Through-holes, 310a . . . Obstacle, 410a . . . Blocking layer, 600 . . . Reed switch, 601 . . . Permanent magnet, 602 . . . Glass pipe, 603a, 603b . . . Magnetic reed.

The invention claimed is:

1. A catheter information managing system, comprising:
a catheter;
an IC tag storing medical equipment information, including both instruction manual information in a plurality of languages setting forth information about use of said catheter and information used for a health insurance claim by a hospital;
a packaging bag containing both the catheter and the IC tag, the packaging bag being a closed packaging bag that is openable;
a management apparatus, the management apparatus including a display unit and a data storage device;
a tag information reader in communication with the management apparatus and configured to receive the medical equipment information transmitted from the IC tag, the IC tag contained within the packaging bag, the tag information reader being fixedly placed only in an operation room or an operation preparation area;
the IC tag being accommodated in an IC tag accommodation portion of the packaging bag, the IC tag having a reed switch and an associated magnet, the reed switch and magnet disposed in such a manner as to oppose to the IC tag,
the packaging bag including a seal portion that seals the packaging bag closed and which is openable, the IC tag being disposed at the seal portion of the packaging, the display unit of the management apparatus operable to display the instruction manual information after receipt by the tag information reader;
the seal portion is broken by opening the packaging bag, the IC tag being configured to begin communicating with the tag information reader when the IC tag is separated from the magnet by opening the packaging bag;
the IC tag transmitting the medical equipment information to the tag information reader,
the tag information reader transmitting the medical equipment information to the management apparatus,
the management apparatus storing the medical equipment information into an IC tag information storage block of the data storage device,
a language specification block stored in the data storage device of the management apparatus operating and referring to a language specification information storage block stored in the data storage device storing language information corresponding to an official language of a country in which the hospital is located, the language specification block acquiring the instruction manual information from the IC tag information storage block in the language corresponding to the language information in the language specification information storage block, and displaying the instruction manual information of the language specification information on the display unit,
the display unit displaying a contents confirmation check column on the display unit,
a contents confirmation check column input presence or absence determination block stored in the data storage device operating to determine whether or not a check mark is inputted into the contents confirmation check column by a user indicating that the user has read the instruction manual information displayed on the display unit, an insurance claim paperwork display block stored in the data storage device of the management apparatus operating to acquire the information used for the health insurance claim by the hospital, the information used for the health insurance claim is stored in the IC tag information storage block and transferred to the management apparatus only when the contents confirmation check column input presence or absence determination block has determined that the check mark is inputted into the contents confirmation check column, the management apparatus preparing a health insurance claim using the information used for the health insurance claim according to a format stored in an insurance claim paperwork basic information storage block stored in the data storage device of the management apparatus.

2. The catheter information management system according to claim 1, wherein the display unit displays a language selection screen image listing the plurality of languages for the user to select one of the plurality of languages as the language in which the instruction manual information is displayed, and the instruction manual information is displayed in the selected language.

3. The catheter information management system according to claim 1, wherein the catheter information management system comprises the language specification information storage block for storing the instruction manual information in the plurality of languages which the instruction manual information is to be displayed on the display unit; and the catheter information management system further comprising a language specification block for receiving user selection of a language from the plurality of languages in the language specification information storage block, and displaying the instruction manual information in the selected language on the display.

4. The catheter information management system according to claim 1, wherein the packaging bag is comprised of a front face and a rear face that are sealed to one another at a seal portion that is sealed closed and is openable, the IC tag being sandwiched between the front face and the rear face.

5. A control method for a catheter information management system, the method comprising:

opening a closed packaging bag, the closed packaging bag containing both a catheter as well as an IC tag, the IC tag storing medical equipment information that includes both instruction manual information in a plurality of languages setting forth information about use of said catheter and information that may be used for a health insurance claim by a hospital, the packaging bag including a seal portion that seals the packaging bag closed and which is openable, the IC tag being disposed at the seal portion of the packaging bag;

the IC tag having a reed switch and an associated magnet, the reed switch and magnet disposed in such a manner as to oppose to the IC tag;

initiating communication with the IC tag with a tag information reader when the IC tag is separated from the magnet by opening the packaging bag, the tag information reader configured to communicate with a management apparatus for receiving the medical equipment information transmitted from the IC tag, the IC tag contained within the packaging bag, the management apparatus including a display unit and a data storage device, and the tag information reader being fixedly placed only in an operation room or an operation preparation area, the IC tag and a magnet being accommodated in an IC tag accommodation portion of the packaging bag;

transmitting the medical equipment information to the management apparatus from the tag information reader;

storing the medical equipment information into an IC tag information storage block in the management apparatus;

storing language information corresponding to an official language of a country in which the hospital is located in a language specification block in the data storage device of the management apparatus operating and referring to a language specification information storage block in the data storage device;

acquiring the instruction manual information of the language specification block from the IC tag information storage block in the language corresponding to the language information in the language specification information storage block, and displaying the instruction manual information of the language specification information on the display unit;

displaying a contents confirmation check column on the display unit, and a contents confirmation check column input presence or absence determination block stored in the data storage device operating to determine whether or not a check mark is inputted into the contents confirmation check column by a user indicating that the user has read the instruction manual information displayed on the display unit;

storing an insurance claim paperwork display block (program) in the data storage device of the management apparatus, which operates to acquire the information used for the health insurance claim by the hospital, the information used for the health insurance claim is stored in the IC tag information storage block and transferred to the management apparatus only when the contents confirmation check column input presence or absence determination block has determined that the check mark is inputted into the contents confirmation check column; and preparing a health insurance claim using the information used for the health insurance claim according to a format stored in an insurance claim paperwork basic information storage block stored in the data storage device of the management apparatus.

6. The control method according to claim 5, further comprising:

displaying on the display a language selection screen image listing the plurality of languages, selecting one of the plurality of languages, and displaying the instruction manual information received by the tag information reader in the selected language.

7. The control method according to claim 5, wherein the catheter information management system comprises the language specification information storage block for storing the instruction manual information in the plurality of languages which the instruction manual information is to be displayed on the display; and receiving user selection of a language from the plurality of languages in the language specification information storage block, and displaying the instruction manual information in the user-selected language on the display.

8. A catheter information managing system, comprising:
a catheter;
an IC tag storing medical equipment information, including both instruction manual information in a plurality of languages setting forth information about use of said catheter and information used for a health insurance claim by a hospital;
a packaging bag containing both the catheter and the IC tag, the packaging bag being a closed packaging bag that is openable, the IC tag being accommodated in an IC tag accommodation portion of the packaging bag, the IC tag having a reed switch and an associated magnet, the reed switch and magnet disposed in such a manner as to oppose to the IC tag, the packaging bag including a seal portion that seals the packaging bag closed and which is openable, the IC tag being disposed at the seal portion of the packaging bag;
a management apparatus, the management apparatus including a display unit and a data storage device;
a tag information reader in communication with the management apparatus and configured to receive the medical equipment information transmitted from the IC tag, the IC tag contained within the packaging bag, and wherein the seal portion is broken by opening the packaging bag, the IC tag being configured to begin communicating with the tag information reader when the IC tag is separated from the magnet by opening the packaging bag;
the display unit of the management apparatus operable to display the instruction manual information after receipt by the tag information reader;
the IC tag transmitting the medical equipment information to the tag information reader;
the management apparatus storing the medical equipment information being received by the tag information reader into an IC tag information storage block;
a language specification block stored in the data storage device of the management apparatus operating and referring to a language specification information storage block stored in the data storage device storing language information corresponding to an official language of a country in which the hospital is located, the language specification block acquiring the instruction manual information from the IC tag information storage block in the language corresponding to the language information in the language specification information storage block, and displaying the instruction manual information of the language specification information on the display unit;
the display unit displaying a contents confirmation check column on the display unit;
a contents confirmation check column input presence or absence determination block stored in the data storage device operating to determine whether or not a check mark is inputted into the contents confirmation check column by a user indicating that the user has read the instruction manual information displayed on the display unit; and
an insurance claim paperwork display block stored in the data storage device of the management apparatus operating to acquire the information used for the health insurance claim by the hospital, the information used for the health insurance claim is stored in the IC tag information storage block and transferred to the management apparatus only when the contents confirmation check column input presence or absence determination block has determined that the check mark is inputted into the contents confirmation check column, and the management apparatus preparing a health insurance claim using the information used for the health insurance claim according to a format stored in an insurance claim paperwork basic information storage block stored in the data storage device of the management apparatus.

9. The catheter information management system according to claim 8, wherein the display unit displays a language selection screen image listing the plurality of languages for the user to select one of the plurality of languages as the language in which the instruction manual information is displayed, and the instruction manual information is displayed in the selected language.

10. The catheter information management system according to claim 8, wherein the catheter information management system comprises the language specification information storage block for storing the instruction manual information in the plurality of languages which the instruction manual information is to be displayed on the display unit; and
a language specification block for receiving user selection of a language from the plurality of languages in the language specification information storage block, and displaying the instruction manual information in the selected language on the display.

11. The catheter information management system according to claim 8, wherein the packaging bag is comprised of a front face and a rear face that are sealed to one another at a seal portion that is sealed closed and is openable, the IC tag being sandwiched between the front face and the rear face.

* * * * *